United States Patent [19]

Dell et al.

[11] 4,042,333
[45] Aug. 16, 1977

[54] APPARATUS AND METHOD FOR GAS ANALYSIS

[75] Inventors: Curtis G. Dell; James A. Williamson, Jr., both of Newark, Del.

[73] Assignee: E. I. Du Pont de Nemours and Company, Wilmington, Del.

[21] Appl. No.: 657,046

[22] Filed: Feb. 11, 1976

Related U.S. Application Data

[63] Continuation of Ser. No. 448,690, March 6, 1974, abandoned.

[51] Int. Cl.$^2$ .................. G01N 1/22; G01N 21/24
[52] U.S. Cl. .................. 23/232 R; 23/232 C; 23/254 R; 73/421.5 R; 73/422 GC; 141/83; 356/246
[58] Field of Search ............ 23/232 R, 232 C, 254 R, 23/232 E, 254 E; 73/422 GC, 421.5 R; 141/83; 137/154; 356/246; 250/576

[56] References Cited

U.S. PATENT DOCUMENTS

| | | | |
|---|---|---|---|
| 3,368,365 | 2/1968 | Harvey, Jr. | 73/422 GC |
| 3,393,551 | 7/1968 | Todd et al. | 73/422 GC |
| 3,507,147 | 4/1970 | Llewellyn | 73/421.5 R |
| 3,698,869 | 10/1972 | Conoon | 23/254 R X |
| 3,718,429 | 2/1973 | Williamson, Jr. | 23/232 R |

Primary Examiner—R.E. Serwin

[57] ABSTRACT

Apparatus and method for gas analysis in which a sample gas is introduced into a high pressure sample cell through a long narrow holding tube, having a volume greater than the volume of the sample cell; and a second gas which will not interfere with the analysis is introduced into the holding tube behind the sample gas, at a pressure sufficient to force a portion of the sample gas contained in the holding tube into the sample cell so that the pressure of the sample gas in the sample cell is increased. An analysis of the sample gas in the sample cell is then made by a suitable technique, preferably by photometric analysis.

8 Claims, 3 Drawing Figures

APPARATUS AND METHOD FOR GAS ANALYSIS

This is a continuation of application Ser. No. 448,690, filed Mar. 6, 1974, and now abandoned.

BACKGROUND OF THE INVENTION

1. Field of the Invention

This invention relates to a method and apparatus for analyzing a gas, and, in particular, to a photometric method and apparatus for analyzing a sample gas for a particular constituent which is present in very low concentrations.

2. Discussion of the Prior Art

Continuous gas analysis techniques, particularly photometric techniques, are sometimes limited to the detection of those components in a gas which are present in concentrations greater than about 100 parts per million (ppm). With the growing concern over atmospheric pollants, particularly nitrogen oxides ($NO_x$) and sulphur dioxide ($SO_2$), however, there is growing desire to be able to determine when small quantities of certain gaseous materials are being introduced into the atmosphere. Hence, there is a need for highly sensitive instruments and techniques capable of detecting low concentrations of certain constituents in a sample gas.

The present invention is applicable, broadly, to instruments and techniques utilizing a variety of detecting methods. It is also applicable broadly to the analysis of any gas constituent for which detection techniques are available. For convenience, however, the following disclosure will be limited to a discussion of a method and apparatus for photometrically determining the $NO_x$ content of a gas. A discussion of such a method and apparatus will suffice to disclose the invention, and it is well within the skill of those skilled in the art to modify the disclosure and apply the invention to methods and apparatus for detecting different gas constituents using different detection devices.

The $NO_2$ content of a gas has previously been photometrically determined using visible radiation falling within the broad $NO_2$ absorption band centered at about 390 NM. NO, however, does not absorb strongly in this wavelength band, and is hence undetectable by this procedure. A technique for analyzing a sample gas for NO is described in U.S. Pat. No. 3,718,429 which issued on Feb. 27, 1973 to James A. Williamson, Jr. and is assigned to the assignee of the present invention. The method described in this patent proceeds by introducing the sample gas into a sample cell, introducing an oxygen-containing gas under pressure into the sample cell to bring about conversion of the NO to $NO_2$, and then detecting NO by observing the increase in absorbance brought about by the conversion of NO to $NO_2$. The use of oxygen to convert NO to $NO_2$ was disclosed by S. W. Nicksic et al in an article in Analytical Chemistry 34, 987 (1962) in which a sample gas was collected in a syringe, mixed with an equal volume of oxygen, then compressed for the prescribed time (usually about 15 minutes) or allowed to stand before being subjected to photometric analysis.

The techniques described above were used to effectuate conversion of NO to $NO_2$ and did not increase the absolute sensitivity of the method and apparatus for $NO_x$. It is the object of this invention to provide a method and apparatus to extend the sensitivity of analytical determinations, particularly photometric determinations, so that analysis, presently limited to a minimum full scale range of 100 parts per million (ppm), can be extended to full scale ranges of the order of 20 ppm.

SUMMARY OF THE INVENTION

This and other objects are accomplished by using an apparatus for analyzing a sample gas comprising a sample cell, means for introducing the sample gas into the sample cell, and means for detecting the presence of at least one component of the sample gas. In particular, the sample cell is a high pressure sample cell; the means for introducing sample gas into the sample cell is a means for introducing the sample gas into the sample cell at a known pressure. The apparatus further comprises a long narrow holding tube, having a known volume greater than the volume of the sample cell, connected between the sample cell and the means for introducing sample gas into the sample cell, so that both the holding tube and the sample cell are filled with sample gas. Finally, the apparatus includes means for introducing a second gas, which will not interfere with the analysis, into the holding tube behind the sample gas at a known pressure sufficient to force at least a portion of the sample gas contained in the holding tube into the sample cell so that the pressure of the sample gas in the sample cell is increased.

In the preferred embodiment, all of the sample gas is forced from the holding tube into the sample cell and the means for detecting the presence of at least one component of the sample gas is a photometric means including a source of radiation, disposed relative to the sample cell to allow radiation to pass through the sample cell, and means for detecting the radiation passing through the sample cell. Furthermore, in the preferred embodiment, the holding tube is in the form of a coil.

It is convenient if the known pressure at which the sample gas is introduced into the sample cell and holding tube is at or near atmospheric pressure, in which case, it is preferred if the pressure at which the second gas is introduced into the holding tube is greater than or equal to about 60 psig.

The method for analyzing a sample gas comprises the steps of:

a. introducing the sample gas into a high pressure sample cell through a long narrow holding tube having a volume greater than the volume of the sample cell;

b. adjusting the pressure of the sample gas in the sample cell and the holding tube to a known value (preferably atmospheric pressure);

c. introducing a second gas which will not interfere with the analysis into the holding tube, behind the sample gas at a pressure (preferably greater than 60 psig) sufficient to force all of the sample gas contained in the holding tube into the sample cell so that the pressure of the sample gas in the sample cell is increased; and d. detecting the pressence of at least one component of the sample gas.

Once again, the detecting step is preferably accomplished by passing radiation through the sample cell with the sample gas therein, and detecting the intensity of the radiation passing through the sample cell. If the apparatus and method is designed for detecting nitrogen oxide, the source of radiation should be a source of radiation between about 410 to about 600 NM, and the apparatus further comprises a means for excluding the radiation below about 410 NM from the cell.

The increased sensitivity of the method and apparatus described above is accomplished by compressing the test gas into the sample cell so that the number of molecules of test gas in the sample cell is increased. There are a number of ways in which the pressure of the sample gas in the sample cell can be increased, the simplest which is to use a pump to force the sample gas into the sample cell. Using a pump, however, gives rise to a number of difficulties. In particular, the sample is generally heated as it passes through the pump and very often the sample is contaminated. The heating problem can be overcome by waiting until the sample gas achieves a given temperature, but this generally decreases the usefulness of the instrument and technique by virtue of the delay involved. Then technique used in the present invention overcomes these difficulties and provides a fast, inexpensive, and effective way to compress the sample gas and increase the sensitivity of the determination.

BRIEF DESCRIPTION OF THE FIGURES

The present invention can best be described by reference to the figures in which.

DETAILED DESCRIPTION OF THE PREFERRED EMBODIMENTS OF THE INVENTION

Figure 1:
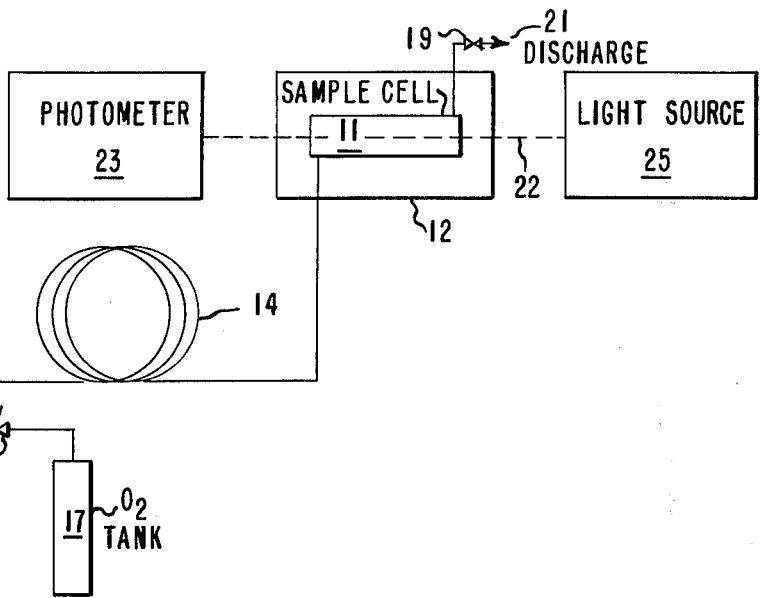
FIG. 1 is a schematic representation of one embodiment of an apparatus of the present invention.

In the preferred embodiment of the present invention, the presence, or preferably the concentration, of a particular constituent in a sample gas is determined photometrically. FIG. 1 shows the basic components of a system used to accomplish a photometric determination according to the present invention.

A sample of any gas which can be analyzed photometrically (usually a gas which absorbs energy in the visible or ultraviolet) is introduced into sample cell 11 through some means to introduce sample gas into the sample cell and holding tube 14. In the embodiment illustrated, the means to introduce sample gas into the sample cell includes sample port 15 and three-way valve 13. The sample cell is a leak tight, high pressure cell designed and built, according to well known techniques, to withstand the pressures used in the present invention and to allow radiation from light source 25 to pass through the sample cell to photometer 23. The sample cell is contained within a heating compartment 12 which is provided to control the temperature to the sample cell, usually within the ranges of about 0 to about 125° C. One suitable sample cell and heating compartment is found in the Du Pont 400 Photometric Analyzer marketed by the Instrument Products Division of the E. I. du Pont de Nemours and Company.

To provide means for decontaminating the sample cell, valve 19 and discharge port 21 are provided. Generally sample gas, or a cleansing gas such as air, forced through the sample cell and discharged through valve 19 and discharge port 21 until all contaminants are removed from the sample cell. At that point, valve 13 is closed and vacuum breaker 65 acts to regulate the pressure of the sample gas in the holding tube and sample cell to a known desired level, normally near atmospheric pressure. Means are also provided to introduce a second gas, which in the embodiment shown is oxygen, into the holding tube 14, behind the sample gas, at a pressure sufficient to force at least a portion of the sample gas contained in the holding tube into the sample cell so that the pressure of the sample gas in the sample cell is increased. In the embodiment illustrated, this means includes a high pressure gas tank 17 and three-way valve 13.

Holding tube 14 is a long narrow holding tube with an internal volume greater than the volume of the sample cell. There is no maximum limit on the volume of the holding tube, but the use to which the apparatus is put dictates that the holding tube should have a volume between about twice about five times the volume of the sample cell. In the preferred embodiment, the holding tube has a volume such that at gas pressures which are readily available and which the sample cell can reasonably withstand (i.e., about 100 psig) all of the sample gas contained in the holding tube and a certain amount of the second gas are forced into the sample cell. This is not absolutely necessary if one is only interested in detecting the presence of small concentrations of a particular constituent such as $SO_2$ in the gas. If an accurate absolute measurement of the concentration of the particular constituent in the sample gas is desired, however the number of sample gas molecules in the sample cell must be accurately known. While pressures can be measured accurately, it is generally more convenient and more accurate to work with known volumes. Therefore, the sample gas is initially allowed to equibrate to atmospheric pressure (an easily achieved pressure) in a sample cell of known volume, and high pressure gas is used to force all of the sample gas contained in the holding tube (again a known volume) into the sample cell. In this way, the number of sample gas molecules in the sample cell can be calculated without concern over the accuracy of the pressure regulator used to introduce the second gas.

Ideally, the pressure of the second gas and volume of the holding tube could be chosen so that only sample gas is introduced into the sample cell. This is both difficult to accomplish and unnecessary. The presence of additional, non-interfering gas in the sample cell along with the sample gas will not effect the analysis. Furthermore, as described in U.S. Pat. No. 3,718,429 where the quantity of interest is the $NO_x$ concentration in sample gas, it is advantageous to allow a certain amount of the second gas (in this case oxygen) into the sample cell. Therefore, while it is possible to use a second gas pressure sufficient to force only a portion of the sample gas contained in the holding tube into the sample cell, and use the known initial pressure of the sample gas in the sample cell and the known pressure of the second gas to calculate the number of sample gas molecules in the sample cell when the analysis takes place, it is much preferred to use a second gas pressure sufficient to sweep all of the sample gas in the holding tube into the sample cell.

The volume of the holding tube should be chosen so that the pressure of the sample gas in the sample cell can be increased significantly; otherwise no significant increase in sensitivity would be achieved. A holding tube with a volume equal to that of the sample cell will give rise to a 2x increase in sensitivity if all the sample gas contained in it is swept into the sample cell. Preferably, however, a holding tube with a much larger volume should be used to achieve higher sensitivity. A tube having a pressure 3x that of the sample cell, used with a second gas pressure of greater than 60 psig, will produce a 4 fold increase in sensitivity.

The diameter of the long narrow holding tube is not critical. It depends on the circumstances involved. In the preferred embodiment, however, one must know the amount of sample gas that is eventually compressed into the sample cell. Therefore, the dimensions of the holding tube and the sample cell must be known accurately along with the initial pressure of the sample gas in the sample cell and holding tube. Depending on the circumstances discussed above, one may also need to know the pressure of the second gas used to compress the sample gas into the sample cell. If the diameter of the holding tube is too large, it is possible that some of the second gas will enter the sample cell without forcing the sample gas into the sample cell before it. If this happens, it will be impossible to accurately determine the amount of sample gas in the sample cell, and therefore impossible to make an accurate determination. On the other hand, if a considerable amount of the second gas is intended to enter the sample cell, this will cause purging of the holding tube and eventually force all of the sample gas contained in the holding tube into the sample cell. Under such circumstances, restrictions on the diameter of the holding tube are less stringent. As a general rule, the holding tube should have an initial diameter of less than about one half inch, but one skilled in the art is quite capable of choosing the dimensions of the holding tube to suit the particular circumstances he desires. The longer and narrower the holding tube, the more control one has over the accuracy of the method, but tubes which are too narrow should be avoided because of pressure drop in the holding coil.

The holding tube can be made from any non-corrosive, non-reactive material. Glass can be used, but glass is generally breakable and therefore less preferred. Any metal, such as stainless steel, can be used as well as any suitable plastic tubing. In the preferred embodiment, the holding tube is a tube made from Teflon* FEP fluorocarbon resin with a nonminal OD of ¼ inches. Because of its inert nature, flexibility and strength, this material makes an ideal holding tube. As shown in FIG. 1, the long narrow holding tube is in the form of a coil. This is not necessary but it does provide a convenient way to put a long narrow holding tube in a small space. The coiled configuration is another reason why a plastic tube is preferred. 6 *. Registered trademark of E. I. du Pont de Nemours & Co.

The gas under as the second gas should be a gas which will not interfere with the analysis. In the embodiment shown, the gas is oxygen. Oxygen generally doesn't interfere with the analysis of gas components, and in the case of NO determinations, it actually causes the conversion of NO to $NO_2$, thereby aiding in the analysis. Any gas which will not interfere with the analysis can be used. Such gases include nitrogen, air or any inert gas such as helium, argon, or neon. Naturally, the gas used should be as free from contaminants as possible.

Figure 2:
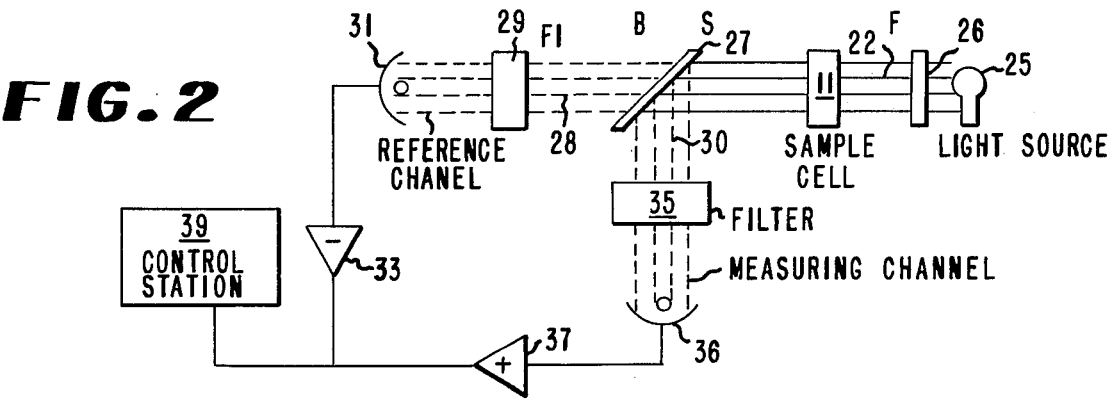
FIG. 2 shows a preferred photometer for use in the present invention.

FIG. 2 shows on particular photometer which can be used in the present invention. This photometer is included in the Du Pont 400 Photometric Analyzer referred to above. Light source 25 may be of any suitable type although a mercury lamp is preferred. An optical filter 26 can be used to filter out undesired radiation. The light then passes through the sample cell 11 and is divided into two components by a beam splitter 27 which in this case is a semitransparent mirror. A portion of the beam 30 goes through filter 35 which blocks all but the measuring radiation. Phototube 36 detects this radiation and its output is positively amplified by logrithmic amplifier 37. In the case of $NO_x$ detection, a wavelength of 436 NM is generally used. The second half 28 of the beam from beam splitter 27 is passed through filter 29 which excludes all but the reference wavelength radiation. Again in $NO_x$ detection, a wavelength of 578 NM is generally used. This reference wavelength radiation responds equally to the scattering in the cell as does the measuring radiation, but is relatively less effected by any absorption which occurs in the sample gas. The radiation passing through filter 29 is detected by phototube 31 whose output is negatively amplified by logrithmic amplifier 33. The output of negative amplifier 33 effectively subtracts the scattering of radiation by the sample cell from the output of the measuring phototube 36, and, thus, allows only the absorption signal to reach control station 39. This data is then available for future use.

Figure 3:
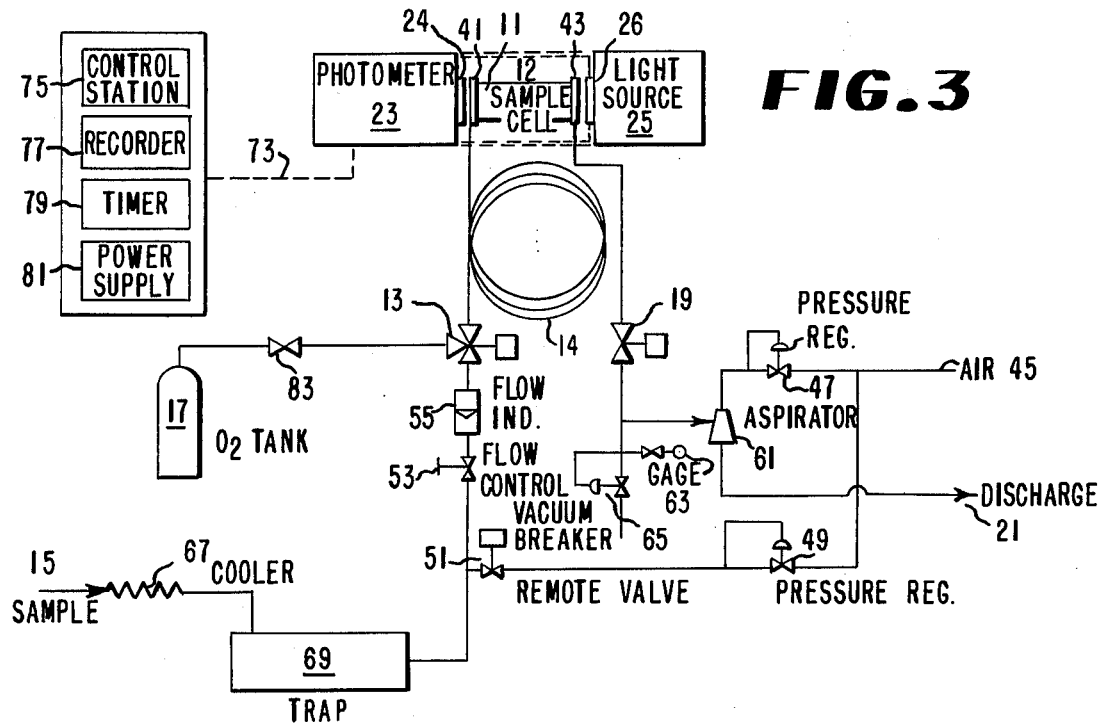
FIG. 3 shows a detailed representation of a preferred embodiment of an apparatus of the present invention.

FIG. 3 depicts a preferred embodiment of the present invention. Photometer 23 and light source 25 are shown with windows 24 and 26 respectively. These windows are made from any suitably transparent material such as Pyrex or quartz. Sample cell 11 also has windows 41 and 43 which are of a suitably transparent material. The entire sample cell is held within a heated compartment 12 which is used to maintain the temperature of the sample cell at the desired level. Power supply 81 powers light source 25, photometer 23 and remote valves 51, 13, 19 & and timer 79 controls the functioning of these valves. Control station 75, recorder 77, timer 79 and power supply 81 are connected to the rest of the system by electrical interconnections 73.

Air which is provided under pressure at 45 has two functions. First, it continually provides gas pressure to aspirator 61 which creates a vacuum in the lines leading back towards the sample cell. This pressure to aspirator 61 is regulated by pressure regulator 47. After passing through aspirator 61, the air is then passed out discharge port 21.

The second function of the air provided at 45 occurs during the apparatus's first cycle of operation. During this cycle, valve 51 is open so that air (at a pressure regulated by regulator 49) is admitted into the line connecting sample cell 12 to sample source 15. Part of the air provided through valve 51 is used to backflush the sample line through trap 69 and cooler 67 to sample source 15. This cleanses the line in preparation for the next measurement. During this first cycle, three way valve 13 is opened to permit a portion of the air provided at 45 to flow into the sample cell 11, and valve 19 is open to permit the flow of air through sample cell 11 and aspirator 61 out discharge opening 21. In this manner, the sample cell and its connecting lines can also be cleansed. Since there is no sample in cell 11 while air is flowing through it during this first cycle, the photometer output is set to 0. After cell 11 and its connecting lines are cleansed, valve 51 closes to prevent air from entering the line connecting sample cell and sample 15 (although the air continues to operate aspirator 61).

The second cycle begins with the closing of valve 51. During the second cycle, as in the first cycle, valves 13 and 19 are opened to allow the passage of the sample gas through valve 13 and holding tube 14 into one side of sample cell 11 and out the other side through valve 19, aspirator 61 and discharge port 21. Aspirator 61 creates a slight vacuum in the sample cell and its connecting lines, which causes the sample gas to flow through cooler 67, trap 69, flow control 53, flow indicator 55, valve 13, holding tube 14, sample cell 11, valve 19, aspirator 61, and out discharge port 21. A vacuum of about 3 inches mercury at the aspirator 61 is sufficient to accomplish this. Cooler 67 is generally employed to reduce the temperature of samples provided from hot sources such as stack gases or auto exhausts, which are warmer than the desired reaction temperature. From cooler 67 the sample gas passes to trap 69 where any moisture that condensed in cooler 67 is removed. Flow indicator 55 need only be occasionally checked to ascertain that flow control 53 is allowing the correct amount of sample to flow into sample cell 11.

Vacuum breaker 65 limits and controls the magnitude of the vacuum within sample cell 11 and its connecting lines, with gauge 63 giving a visual indication of the vacuum. Vacuum breaker 65 bleeds in sufficient air to reduce the vacuum created by aspirator 61 to the desired magnitude. Because the pressure within sample cell 11 and holding coil 14 is thus accurately controlled, the amount of sample is also accurately controlled. Accordingly, even while samples flow through sample cell 11, higher concentration of the particular constituent in the sample gas may be accurately determined by light source 25 and photometer 23.

When the sample gas completely fills sample cell 11 and holding tube 14, valve 13 closes. Valve 19, however, remains open for a period of time sufficient for the pressure of the sample gas (and hence the amount of sample) in the sample cell 11 to be regulated and controlled by vacuum breaker 65. Then valve 19 closes and isolates the sample within sample cell 11 and holding tube 14. In the preferred embodiment, the pressure of the sample gas in the sample cell and the holding tube is adjusted to 3 inches of Hg vacuum with respect to atmospheric pressure.

During the succeeding third cycle, valves 13 and 83 open to allow oxygen from tank 17 to flow into holding tube 14 behind the sample gas. The pressure of the oxygen passed to valve 13 through control valve 83 is regulated so that all of the sample gas contained in holding tube 14 is forced into sample cell 11. Depending upon the type of analysis involved, the pressure of the second gas may be regulated so that, in addition to the sample gas contained in holding tube 14, a considerable amount of the second gas may also be forced into sample cell 11. Such is the case in the $NO_x$ determination described in U.S. Pat. No. 3,718,429. After the desired amount of oxygen has gone through valve 13, valve 13 is closed to isolate the mixture of sample gas and second gas in sample cell 11.

After sufficient time has elapsed to allow the desired reaction to take place, light source 25 and photometer 23 measure the amount of the desired substance in the sample gas. After the analysis has taken place, valves 51, 13 and 19 are opened to admit air into the sample cell, the holding tube and the connecting lines. This prepares the apparatus for the next determination.

EXAMPLE

The following example was run on a Du Pont 411 Photometeric Analyzer (which has a sample cell volume of 15.71 cubic inches) equipped with a 212 foot, nominal one quarter inch OD, holding tube made from Teflon FEP fluorocarbon resin. The holding tube has an internal volume of 68.89 cubic inches so that the total volume of the cell and tubing is 84.60 cubic inches.

Using the procedure outlined with regard to FIGS. 3 above, the sample cell and holding tube were first purged with air, and then filled with a standard sample gas containing 1,000 ppm of NO. The pressure of the sample gas in the sample cell and holding tube was adjusted to atmospheric pressure and 84.60 cubic inches of sample gas was isolated in the holding tube and sample cell. At that point, oxygen at a pressure of 110 psig (124.7 psia) was introduced into the holding tube behind the sample gas, forcing the sample gas and a certain amount of oxygen into the sample cell. The sample volume when compressed to 110 psig was 9.97 cubic inches, and the theoretical increase in sensitivity (the ratio of the total volume of the cell plus holding tube to the volume of the cell itself) was calculated to be 5.388. The sample cell was irradiated with radiation in the 410–600 NM range. After waiting several minutes for the conversion of nitrogen oxide to $NO_2$, the increase in absorbance over that at atmospheric pressure was measured. An increase sensitivity of 5.4 to 5.7 was observed over the sensitivity obtained when only 15.71 cubic inches of sample gas was contained in the sample cell. This result was reproducible to within ±1%.

We claim:

1. A method for analyzing a sample gas, comprising the steps of:
    a. introducing the sample gas into a high pressure sample cell through a long narrow holding tube having a volume greater than the volume of the sample cell;
    b. adjusting the pressure of the sample gas in the sample cell and the holding tube to a known value;
    c. closing off the sample cell at the end opposite the holding tube;
    d. introducing a second gas, which will not interfere with the analysis, into the holding tube, behind the sample gas, at a pressure sufficient to force all of the sample gas contained in the holding tube into the sample cell adding to the sample gas originally contained in the sample cell so that the pressure of the sample gas in the sample cell is increased; and
    e. detecting the presence of at least one component of the sample gas.

2. A method for photometrically analyzing a sample gas, comprising the steps of:
    a. introducing the sample gas into a high pressure sample cell through a long, narrow holding tube having a volume greater than the sample cell;
    b. adjusting the pressure of the sample gas in the sample cell and holding tube to a known value;
    c. closing off the sample cell at the end opposite the holding tube;
    d. introducing a second gas, which will not interfere with the analysis, into the holding tube, behind the sample gas, at a pressure sufficient to force all of the sample gas contained in the holding tube into the sample cell adding to the sample gas originally contained in the sample cell so that the pressure of the sample gas in the sample cell is increased; and
    e. passing radiation through the sample cell with the sample gas therein, and
    f. detecting the intensity of the radiation passing through the sample cell.

3. The method of claim 2 wherein the step of introducing a second gas into the holding tube is accomplished at a pressure greater than or equal to about 60 psig.

4. The method of claim 2 further comprising the step of maintaining the sample cell at a substantially constant temperature.

5. The method of claim 2 wherein the step of passing radiation through the sample cell is accomplished by passing radiation of between about 410 to about 600 NM through the sample cell.

6. A method of photometrically analyzing a sample gas to determine the amount of $NO_x$ in the sample gas, comprising the steps of:
   a. introducing the sample gas into a high pressure sample cell through a long, narrow holding tube having a volume greater than the sample cell;
   b. maintaining the temperature of the sample cell and holding tube at a substantially constant temperature;
   c. adjusting the pressure of the sample gas in the sample cell and holding tube to a known value;
   d. closing off the sample cell at the end opposite the holding tube;
   e. introducing an oxygen containing gas into the holding tube behind the sample gas at a pressure sufficient to force all of the sample gas in the holding tube and at least some oxygen containing gas into said sample cell adding to the sample gas originally contained in the sample cell;
   f. maintaining the temperature of said sample cell at a known temperature;
   g. passing radiation of between about 410 to about 600 NM through said sample cell with said sample gas an said oxygen containing gas therein; and
   h. detecting the intensity of the radiation passing through the sample cell.

7. The method of claim 6 wherein radiation of about 436 NM is passed through said sample cell and additionally radiation of about 578 NM is passed through said sample cell as a reference.

8. The method of claim 6 wherein said oxygen-containing gas is substantially pure oxygen.

* * * * *